(12) United States Patent
Kaneko et al.

(10) Patent No.: US 9,874,530 B2
(45) Date of Patent: Jan. 23, 2018

(54) METHOD OF MEASURING CROSSLINK DENSITIES IN SULFUR-CONTAINING POLYMER COMPOSITE MATERIAL

(71) Applicant: SUMITOMO RUBBER INDUSTRIES, LTD., Kobe-shi, Hyogo (JP)

(72) Inventors: Fusae Kaneko, Kobe (JP); Hiroyuki Kishimoto, Kobe (JP)

(73) Assignee: SUMITOMO RUBBER INDUSTRIES, LTD., Kobe-shi, Hyogo (JP)

( * ) Notice: Subject to any disclaimer, the term of this patent is extended or adjusted under 35 U.S.C. 154(b) by 120 days.

(21) Appl. No.: 14/825,642

(22) Filed: Aug. 13, 2015

(65) Prior Publication Data
US 2016/0077024 A1    Mar. 17, 2016

(30) Foreign Application Priority Data

Sep. 11, 2014  (JP) ................... 2014-185411
Jun. 29, 2015  (JP) ................... 2015-130060

(51) Int. Cl.
  *G01N 23/087*  (2006.01)
  *G01N 33/44*   (2006.01)
  *G01N 23/06*   (2006.01)

(52) U.S. Cl.
  CPC ......... *G01N 23/087* (2013.01); *G01N 23/063* (2013.01); *G01N 33/445* (2013.01); *G01N 2223/203* (2013.01)

(58) Field of Classification Search
  CPC ....... G01N 2223/203; G01N 2223/041; G01N 2223/601; G01N 2223/615; G01N 2223/627; G01N 23/087
  See application file for complete search history.

(56) References Cited

U.S. PATENT DOCUMENTS

| 6,176,945 B1 * | 1/2001 | Bancroft | C23C 22/03 |
| | | | 148/250 |
| 7,431,969 B2 * | 10/2008 | Gleason | B05D 1/60 |
| | | | 427/255.28 |
| 2013/0226470 A1 * | 8/2013 | Kaneko | G01N 23/00 |
| | | | 702/34 |

FOREIGN PATENT DOCUMENTS

| JP | 2013-108800 | * | 6/2013 |
| JP | 2013108800  | * | 6/2013 |

OTHER PUBLICATIONS

Machine Translation of JP 2013-108800.*

(Continued)

*Primary Examiner* — David J Makiya
*Assistant Examiner* — Soorena Kefayati
(74) *Attorney, Agent, or Firm* — Birch, Stewart, Kolasch & Birch, LLP

(57) ABSTRACT

Provided is an evaluation method that provides detailed information on the crosslink densities in sulfur-containing polymer composite materials. The present invention relates to a method of measuring crosslink densities in a sulfur-containing polymer composite material, the method including: a measurement step of irradiating the sulfur-containing polymer composite material with high intensity X-rays and measuring an X-ray absorption spectrum of the composite material while varying the energy of the X-rays; a visualization step of determining the three-dimensional structure of sulfur atoms in the sulfur-containing polymer composite material by the reverse Monte Carlo method from the X-ray absorption spectrum; and a calculation step of calculating, from the three-dimensional structure of sulfur atoms, a crosslink density for each number of sulfur atoms bonded.

3 Claims, 2 Drawing Sheets

(56) References Cited

OTHER PUBLICATIONS

Hideo Nakauchi, Analysis of Crosslinking Structure by Compressive Property of Swollen Rubber (Report No. 1)—Test Method Development, 1987, vol. 60, pp. 267-272.*

Nakauchi et al., "Anaysis of Crosslinking Structure by Compressive Property of the Swollen Rubber (No. 1 Report)," The Journal of the Society of Rubber Science and Technology, Japan (1987), vol. 60, No. 5, pp. 267-272, with English abstract (on p. 272).

* cited by examiner

METHOD OF MEASURING CROSSLINK DENSITIES IN SULFUR-CONTAINING POLYMER COMPOSITE MATERIAL

TECHNICAL FIELD

The present invention relates to a method of measuring crosslink densities in a sulfur-containing polymer composite material.

BACKGROUND ART

A known method for analyzing the sulfur crosslinked structure of a rubber vulcanizate crosslinked with a sulfur-containing compound such as sulfur vulcanizing agent is to selectively cleave crosslinks by a reagent such as $LiAlH_4$ or propane-2-thiol, and calculate, from the amount of swelling before and after the cleavage, the crosslink densities [mol/cm$^3$] of monosulfide bonds (R—$S_1$—R), disulfide bonds (R—$S_2$—R), and polysulfide bonds (R—$S_n$—R (n≥3)) in the rubber vulcanizate according to the Flory-Rehner equation (see, for example, Non Patent Literature 1).

CITATION LIST

Non Patent Literature

Non Patent Literature 1: Hideo Nakauchi, and other four persons, "NIPPON GOMU KYOKAISHI", 1987, Vol. 60, No. 5, pp. 267-272

SUMMARY OF INVENTION

Technical Problem

It is considered that if the sulfur crosslinked structure of a sulfur-containing polymer composite material such as a rubber vulcanizate crosslinked with a sulfur-containing compound can be controlled, then the properties required of the sulfur-containing polymer composite material, such as mechanical properties, can be precisely controlled. Therefore, analyzing the sulfur crosslinked structure of a sulfur-containing polymer composite material is very important in controlling the required properties.

Although, as described above, a method for analyzing the sulfur crosslinked structure of a rubber vulcanizate has been conventionally known, the conventional method can only calculate crosslink densities of three types of sulfide bonds, i.e., monosulfide bonds (R—$S_1$—R), disulfide bonds (R—$S_2$—R), and polysulfide bonds (R—$S_n$—R (n≥3)), in the rubber vulcanizate. Moreover, propane-2-thiol, which preferentially cleaves polysulfide bonds (R—$S_n$—R (n≥3)), often cannot be used because of its strong odor. For this reason, the sulfur crosslinked structure has often been analyzed by calculating the crosslink densities of the two types: monosulfide bonds (R—$S_1$—R) and polysulfide bonds (R—$S_n$—R (n≥2)) including disulfide bonds. Such a method, however, cannot reveal the details of polysulfide bonds (R—$S_n$—R (n=2, 3, 4, 5, 6, 7, 8)) and is insufficient to control the required properties by controlling the sulfur crosslinked structure. Thus, there is still room for improvement to analyze the sulfur crosslinked structure in greater detail.

The present invention aims to solve the above problems and provide an evaluation method that provides detailed information on the crosslink densities in sulfur-containing polymer composite materials.

Solution to Problem

The present invention relates to a method of measuring crosslink densities in a sulfur-containing polymer composite material, the method including:
a measurement step of irradiating the sulfur-containing polymer composite material with high intensity X-rays and measuring an X-ray absorption spectrum of the composite material while varying the energy of the X-rays;
a visualization step of determining a three-dimensional structure of sulfur atoms in the sulfur-containing polymer composite material by a reverse Monte Carlo method from the X-ray absorption spectrum; and
a calculation step of calculating, from the three-dimensional structure of sulfur atoms, a crosslink density for each number of sulfur atoms bonded.

The composite material is preferably scanned with the X-rays in an energy range of 2300 to 4000 eV to measure an X-ray absorption spectrum near the K-shell absorption edge of sulfur.

The X-rays preferably have a number of photons of $10^7$ photons/s or more, and a brilliance of $10^{10}$ photons/s/mrad$^2$/mm$^2$/0.1% bw or higher.

Advantageous Effects of Invention

The method of the present invention measures crosslink densities in a sulfur-containing polymer composite material by irradiating the sulfur-containing polymer composite material with high intensity X-rays and measuring an X-ray absorption spectrum of the composite material while varying the energy of the X-rays; determining the three-dimensional structure of sulfur atoms in the sulfur-containing polymer composite material by the reverse Monte Carlo method from the X-ray absorption spectrum; and calculating, the three-dimensional structure of sulfur atoms, a crosslink density for each number of sulfur atoms bonded. Accordingly, detailed information on the crosslink densities in the sulfur-containing polymer composite material can be obtained.

DESCRIPTION OF EMBODIMENTS

Figure 1:
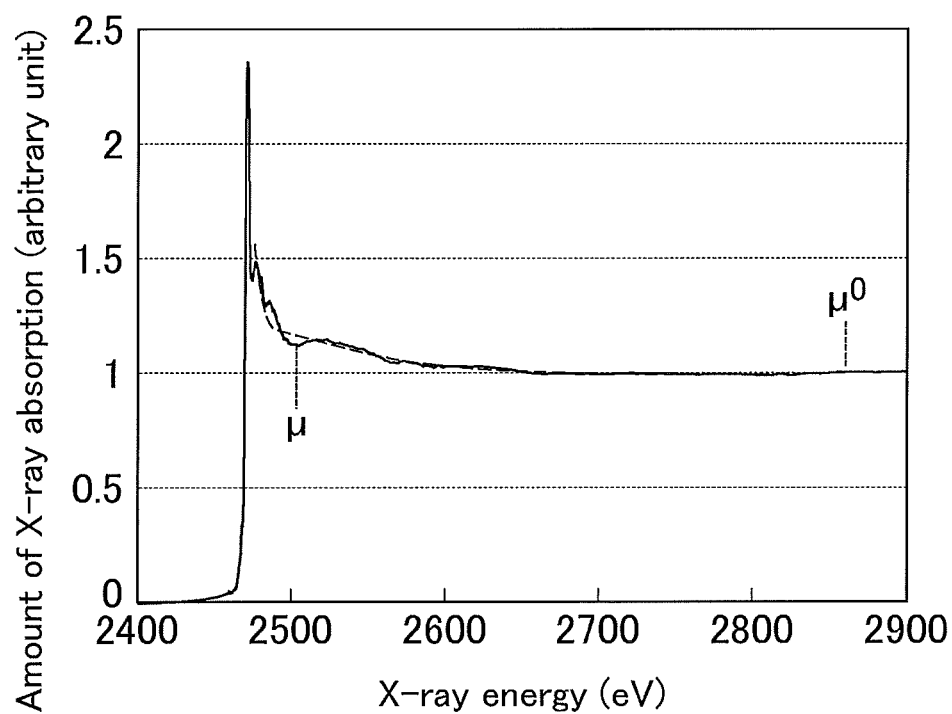
FIG. 1 is a graph showing an X-ray absorption spectrum near the K-shell absorption edge of sulfur obtained in Example 1.

The present invention relates to a method of measuring crosslink densities in a sulfur-containing polymer composite material, the method including a measurement step of irradiating the sulfur-containing polymer composite material with high intensity X-rays and measuring an X-ray absorption spectrum of the composite material while varying the energy of the X-rays; a visualization step of determining the three-dimensional structure of sulfur atoms in the sulfur-containing polymer composite material by the reverse Monte Carlo method from the X-ray absorption spectrum; and a calculation step of calculating, from the three-dimensional structure of sulfur atoms, a crosslink density for each number of sulfur atoms bonded. In the present invention, the number of sulfide bonds for each of different sulfide bonds having 1 to 8 sulfur atoms (R—$S_n$—R (1≤n≤8)) can be determined by fitting the X-ray absorption spectrum obtained in the measurement step by the reverse Monte Carlo method. From the obtained data, a crosslink density can be calculated for each number of sulfur atoms bonded. Therefore, more detailed information on the crosslink densities in the sulfur-containing polymer composite material can be obtained than in the prior art.

The measurement method of the present invention may include other steps as long as it includes the above steps.

The measurement step in the present invention includes irradiating a sulfur-containing polymer composite material (hereinafter, also referred to simply as "sample") with high intensity X-rays and measuring an X-ray absorption spectrum of the composite material while varying the energy of the X-rays. In the measurement step, an X-ray absorption spectrum is measured, for example, by XAFS (X-ray absorption fine structure: near-edge X-ray absorption fine structure) spectroscopy.

The XAFS near the sulfur K-shell absorption edge is useful to measure crosslink densities in sulfur-containing polymer composite materials such as rubber materials formed using sulfur-containing compounds (e.g. sulfur vulcanizing agent).

The XAFS spectroscopy measures the amount of X-rays absorbed by a target atom by irradiation with X-rays, and allows the chemical state (bonding) to be analyzed in detail by using the fact that X-rays energy absorption varies depending on the chemical state (bonding). However, sulfur-containing polymer composite materials contain various types of sulfur crosslinks with different bond lengths, such as monosulfide, disulfide, and polysulfide bonds. The energy peaks of these bonds are detected close to each other in spectra. Moreover, in the case that zinc oxide is added, zinc sulfide is then generated, and its spectrum is also observed. Since the chemical states of sulfur atoms in sulfur-containing polymer composite materials are complicated as described above, XAFS spectra obtained from the sulfur-containing polymer composite materials tend to be broader than those of polymer materials free of sulfur components. Therefore, more accurate measurements are required to analyze the sulfur-containing polymer composite materials. For highly accurate measurements by XAFS spectroscopy, high intensity X-rays may be used.

Furthermore, in the XAFS analysis, the X-ray absorption near edge structure (XANES) region, which involves peaks within about 50 eV of the absorption edge (the energy at which a rise in absorption is observed) onset, and the extended X-ray absorption fine structure (EXAFS) region, which involves weaker oscillations at higher energies. In the XANES region, when a sample is irradiated with X-rays near the absorption edge of a target atom, a transition in which a core-level electron is excited occurs. Therefore, the XANES region provides information about the type of atom to which the target atom is bonded (i.e., chemical state). In the EXAFS region, on the other hand, the core electron becomes free from the nucleus and ejected as a photoelectron. Since the ejected photoelectron can be treated as a wave, the photoelectron wave is backscattered by neighboring atoms, if present, to cause interference. Therefore, the EXAFS region provides information on the number of atoms around the central atom, the species of atom, the distance between atoms, and the like. In the present invention, the X-ray absorption spectrum used in the visualization step described later is preferably an EXAFS spectrum (hereinafter, also referred to as "EXAFS oscillation") obtained by XAFS measurements near the sulfur K-shell absorption edge.

The sulfur-containing polymer composite material used in the measurement method of the present invention may be any polymer composite material that is crosslinked with a sulfur-containing compound such as sulfur vulcanizing agent, and has a sulfur crosslinked structure. Examples include conventionally known sulfur crosslinked rubber compositions such as vulcanized rubber compositions obtained by crosslinking of rubber compositions that contain a sulfur-containing compound such as sulfur vulcanizing agent, a rubber component, and other compounding materials.

Examples of the sulfur-containing compound include sulfur powder, precipitated sulfur, colloidal sulfur, insoluble sulfur, highly dispersible sulfur, and other sulfur vulcanizing agents.

Examples of the rubber component include diene rubbers such as natural rubber (NR), polyisoprene rubber (IR), polybutadiene rubber (BR), styrene butadiene rubber (SBR), acrylonitrile butadiene rubber (NBR), chloroprene rubber (CR), butyl rubber (IIR), halogenated butyl rubber (X-IIR), and styrene isoprene butadiene rubber (SIBR). Further, the rubber component may contain one or more modifying groups such as a hydroxyl group or amino group. In addition, various elastomers may be used as the rubber component.

Furthermore, composite materials of the rubbers listed above and one or more resins may also be used as the rubber component. The resin is not particularly limited, and examples include those commonly used in the rubber industrial field, such as C5 aliphatic petroleum resins, cyclopentadiene petroleum resins, and other petroleum resins.

The sulfur-containing polymer composite material may appropriately contain compounding materials known in the rubber field, including, for example, filler such as carbon black or silica, a silane coupling agent, zinc oxide, stearic acid, an antioxidant, wax, oil, a vulcanizing agent other than sulfur, a vulcanization accelerator or the like. Such a rubber material (rubber composition) may be prepared by performing a known mixing process, vulcanization process, and the like. Examples of the rubber material include vulcanized rubber materials for tires (vulcanized rubber compositions for tires).

Specifically, for example, the following transmission method, fluorescence method, and electron yield method are typically used as the method of irradiating a sample with high intensity X-rays and measuring an X-ray absorption spectrum while varying the energy of the X-rays.

(Transmission Method)

This is a method of detecting the intensity of X-rays having transmitted through a sample. For the measurement of the intensity of transmitted light, for example, a photo-diode array detector may be used.

(Fluorescence Method)

This is a method of detecting fluorescent X-rays generated when a sample is irradiated with X-rays. A Lytle detector, semiconductor detector, or the like is used in the detection. In the case of the transmission method, if the X-ray absorption of an element contained in a small amount in a sample is measured, then a spectrum with a poor S/B ratio is obtained because the signal is small while the background is high due to X-ray absorption by an element contained in a large amount in the sample. In contrast, in the case of the fluorescence method (especially when an energy dispersive detector or the like is used), only the fluorescent X-rays from a target element can be measured, and therefore the element contained in a large amount has a small influence. For this reason, the method is effective to measure an X-ray absorption spectrum of an element contained in a small amount. In addition, since fluorescent X-rays have high penetrating power (low interaction with substances), fluorescent X-rays generated inside the sample can be detected. Thus, the method is the second most suitable method for obtaining bulk information after the transmission method.

(Electron Yield Method)

This is a method of detecting a current flowing when a sample is irradiated with X-rays. Thus, the sample needs to be an electrically conductive material. The method also features surface sensitivity (information at a depth of approximately several nanometers below the sample surface). Irradiation of a sample with X-rays causes escape of electrons from elements. Since electrons have a great interaction with substances, their mean free path in a substance is short.

Thus, the transmission method, which is a basic XAFS measurement method that measures X-ray absorption by detecting the intensity of incident light and the intensity of X-rays transmitted through a sample, provides bulk information on the sample. Therefore, the method is characteristically difficult to use in measurements of compounds, unless they are at concentrations of not lower than a certain level (for example, several percent by weight or higher). The electron yield method, which is a surface-sensitive method, provides information at a depth of approximately several tens of nanometers below the sample surface. On the other hand, the fluorescence method is characterized by providing information at some great depth below the surface as compared with the electron yield method, and also by being able to measure compounds even at low concentrations. In the present invention, the fluorescence method is suitably used.

The fluorescence method is then described in more detail below.

The fluorescence method, which includes monitoring fluorescent X-rays generated when a sample is irradiated with X-rays, indirectly determines X-ray absorption from the intensity of fluorescent X-rays according to the proportional relationship between the amount of X-ray absorption and the intensity of fluorescent X-rays. The fluorescence method is often carried out using an ionization chamber or a semiconductor detector such as a silicon drift detector (SDD) or silicon strip detector (SSD). Although the use of an ionization chamber provides relatively easy measurements, it has difficulty in energy separation, and may also increase the background because X-rays scattered from a sample or fluorescent X-rays from an element other than a target element can enter the ionization chamber. Therefore, a solar slit or a filter needs to be placed between the sample and the detector. On the other hand, the use of SDD or SSD allows for high sensitive measurements and energy separation, and therefore it can detect only the fluorescent X-rays from a target element, thereby providing measurements with good S/B ratios.

The X-rays used in the measurement step preferably have a number of photons of $10^7$ photons/s or more. Such X-rays enable highly accurate measurements. The number of photons of the X-rays is more preferably $10^9$ photons/s or more. The upper limit of the number of photons of the X-rays is not particularly limited, but the X-ray intensity used is preferably low enough not to cause radiation damage.

The X-rays used in the measurement step preferably have a brilliance of $10^{10}$ photons/s/mrad$^2$/mm$^2$/0.1% bw or higher.

The XAFS spectroscopy, which includes scanning the X-ray energy, requires a continuous X-ray generator as a light source. In addition, X-ray absorption spectra with high S/N and S/B ratios are required for detailed analysis of the chemical state. Therefore, most suitable for XAFS measurements are synchrotrons which are continuous X-ray sources and emit X-rays having a brilliance of $10^{10}$ photons/s/mrad$^2$/mm$^2$/0.1% bw or higher, where the "bw" refers to a band width of X-rays emitted from a synchrotron. The brilliance of the X-rays is more preferably $10^{11}$ photons/s/mrad$^2$/mm$^2$/0.1% bw or higher. The upper limit of the brilliance of the X-rays is not particularly limited, but the X-ray intensity used is preferably low enough not to cause radiation damage.

In the measurement step, the composite material is suitably scanned with the X-rays in an energy range of 2300 to 4000 eV. By scanning in the above range an X-ray absorption spectrum near the sulfur K-shell absorption edge can be measured, and information on the chemical states of sulfur atoms in the sample can be obtained. The energy range is more preferably 2350 to 3500 eV.

The visualization step in the present invention includes determining the three-dimensional structure of sulfur atoms in the sulfur-containing polymer composite material by the reverse Monte Carlo method from the X-ray absorption spectrum obtained in the measurement step.

The reverse Monte Carlo method estimates the three-dimensional structure consistent with the neutron or X-ray diffraction data, and may also be used for EXAFS spectra. The EXAFS oscillation $\chi(k)$ obtained by XAFS measurements near the sulfur K-shell absorption edge is represented by the formula (1) below using EXAFS oscillation $\chi_1(k, r)$ corresponding to the contribution of a single scattering atom at a distance r.

$$\chi(k) = \sum_\beta 4\pi\rho \int_0^\infty r^2(g_{\alpha\beta}(r) - 1)\chi_1(k, r)dr \quad (1)$$

($g_{\alpha\beta}(r)$: Radial distribution function, $\rho$: Electron density, $k$: Wave number)

In the reverse Monte Carlo method, first, an expected three-dimensional configuration of particles is taken as an initial configuration, from which EXAFS oscillation $E_{calc}(k)$ is calculated and then the configuration of particles is changed using random numbers or the like, followed by the calculation of $E_{calc}(k)$. The process is repeated until the $E_{calc}(k)$ is consistent with the actual EXAFS oscillation $E_{exp}(k)$. Specifically, the structure (configuration) is determined by repeating the calculation until $X^2$ represented by the formula (2) below converges.

The $E_{calc}(k)$ can be calculated from each three-dimensional configuration based on previous calculations using an ab initio self-consistent real space multiple scattering calculation program based on an all-electron, real space relativistic Green's function formalism such as FEFF.

$$X^2 = \frac{\sum_k (E_{exp}(k) - E_{calc}(k))^2}{\sigma_{std}^2} \quad (2)$$

($\sigma_{std}^2$: Standard deviation)

In this way, the three-dimensional structure of sulfur atoms in the sulfur-containing polymer composite material can be determined by the reverse Monte Carlo method from the X-ray absorption spectrum obtained in the measurement step.

The calculation step in the present invention includes calculating, from the three-dimensional structure of sulfur atoms determined in the visualization step, a crosslink density for each number of sulfur atoms bonded. Specifically, the number of sulfide bonds for each of different sulfide bonds having 1 to 8 sulfur atoms (R—$S_n$—R ($1 \leq n \leq 8$)) is counted based on the three-dimensional structure of sulfur atoms determined in the visualization step, and then the crosslink densities of the different sulfide bonds (R—$S_n$—R ($1 \leq n \leq 8$)) can be calculated according to the following formula (3):

$$\text{Crosslink density [mol/cm}^3\text{]} = \frac{\text{Number of bonds}}{6.02 \times 10^{23} \times (\text{Side of BOX [cm]})^3}. \tag{3}$$

The size of the BOX in the formula (3) is automatically determined from the number density of sulfur atoms and the number of sulfur particles in the sample.

The number density of sulfur atoms in the sample can be calculated from the amount of sulfur atoms involved in crosslinking in the sample and the density of the sample, as described in examples described later.

The number of sulfur particles can be arbitrarily set. A larger number is preferred because it results in more accurate results (crosslink density). However, too large a number results in complicated and huge calculations, which are substantially impossible to carry out. Therefore, the number of sulfur particles needs to be set as large as possible, provided that the calculations can be carried out.

The number of sulfur particles may be set, for example, by the following method.

Since the sample presumably contains a polysulfide bond having eight sulfur atoms, the BOX needs to be sized to accommodate the polysulfide bond. Then, since a structurally stable polysulfide bond determined by molecular orbital calculations has an S—S interatomic distance of 2.0 to 2.4 Å, the length of the side of the BOX needs to be at least 16.8 Å (=2.4 [Å]×(8−1)). Therefore, the number of particles is set so that the BOX is sized to be 16.8 Å or longer on a side.

As described above, the method of measuring crosslink densities in a sulfur-containing polymer composite material of the present invention can be used to provide more detailed information on the crosslink densities in sulfur-containing polymer composite materials than in the prior art.

EXAMPLES

The present invention will be specifically described by reference to examples which, however, are not intended to limit the scope of the present invention.

[Preparation of Sample]

A 1.7-L Banbury mixer produced by KOBE STEEL, LTD. was filled to 58% of its volume with materials other than sulfur and a vulcanization accelerator in accordance with the following formulation. The materials were mixed at 80 rpm to 140° C. (step 1). To the resulting mixed mass obtained in step 1 were added the sulfur and the vulcanization accelerator according to the following formulation, and they were vulcanized at 160° C. for 20 minutes to provide a rubber sample (step 2).

The formulation is as follows: 50 parts by mass natural rubber, 50 parts by mass polybutadiene rubber, 60 parts by mass carbon black, 5 parts by mass oil, 2 parts by mass antioxidant, 2.5 parts by mass wax, 3 parts by mass zinc oxide, 2 parts by mass stearic acid, 1.2 parts by mass sulfur powder, and 1 part by mass vulcanization accelerator. The materials used are listed below.

Natural rubber: TSR20
Polybutadiene rubber: BR150B produced by UBE INDUSTRIES, LTD.
Carbon black: SHOBLACK N351 produced by Cabot Japan K.K.
Oil: Process X-140 produced by Japan Energy Corporation
Antioxidant: NOCRAC 6C (N-1,3-dimethylbutyl-N'-phenyl-p-phenylenediamine) produced by Ouchi Shinko Chemical Industrial Co., Ltd.
Wax: OZOACE 0355 produced by Nippon Seiro Co., Ltd.
Zinc oxide: Ginrei R produced by TOHO ZINC CO., LTD.
Stearic acid: Tsubaki produced by NOF Corporation
Sulfur powder (containing 5% of oil): 5% oil-treated sulfur powder (soluble sulfur containing 5% by mass of oil) produced by Tsurumi Chemical Industry Co., Ltd.
Vulcanization accelerator: Nocceler CZ (N-cyclohexyl-2-benzothiazylsulfenamide) produced by Ouchi Shinko Chemical Industrial Co., Ltd.

Example 1

(1) XAFS Analysis

The obtained rubber sample was subjected to XAFS measurements near the sulfur K-shell absorption edge to obtain an XAFS spectrum.

FIG. 1 shows the obtained XAFS spectrum. In FIG. 1, $\mu$ represents absorbance, and $\mu^0$ represents the absorbance when the target atom is isolated.

The XAFS measurements were carried out in accordance with the following measurement conditions.
(Used Device)
XAFS: XAFS spectrometer in B-branch of BL27SU at the SPring-8
(Measurement Conditions)
Brilliance: $1 \times 10^{16}$ photons/s/mrad$^2$/mm$^2$/0.1% bw
Number of photons: $5 \times 10^{10}$ photons/s
Monochromator: Crystal monochromator
Detector: SDD (silicon drift detector)
Measurement method: Fluorescence method
Energy range: 2360 to 3500 eV EXAFS oscillation was extracted from the obtained XAFS spectrum. The EXAFS oscillation x(k) was extracted from the XAFS spectrum according to the following formula (4):

$$\chi(k) = \frac{\mu(k) - \mu^0(k)}{\mu^0(k)} \tag{4}$$

wherein $\mu(k)$ represents absorbance, and $\mu^0(k)$ represents the absorbance when the target atom is isolated.

Figure 2:
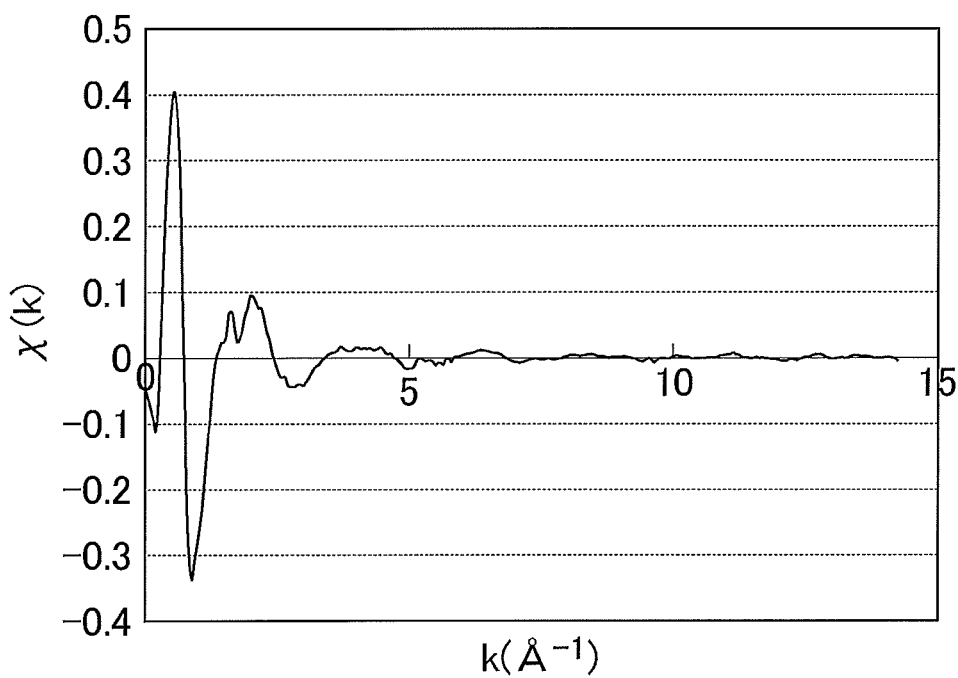
FIG. 2 is a graph showing, in k-space, an EXAFS oscillation spectrum extracted from the X-ray absorption spectrum near the K-shell absorption edge of sulfur obtained in Example 1.
Figure 3:
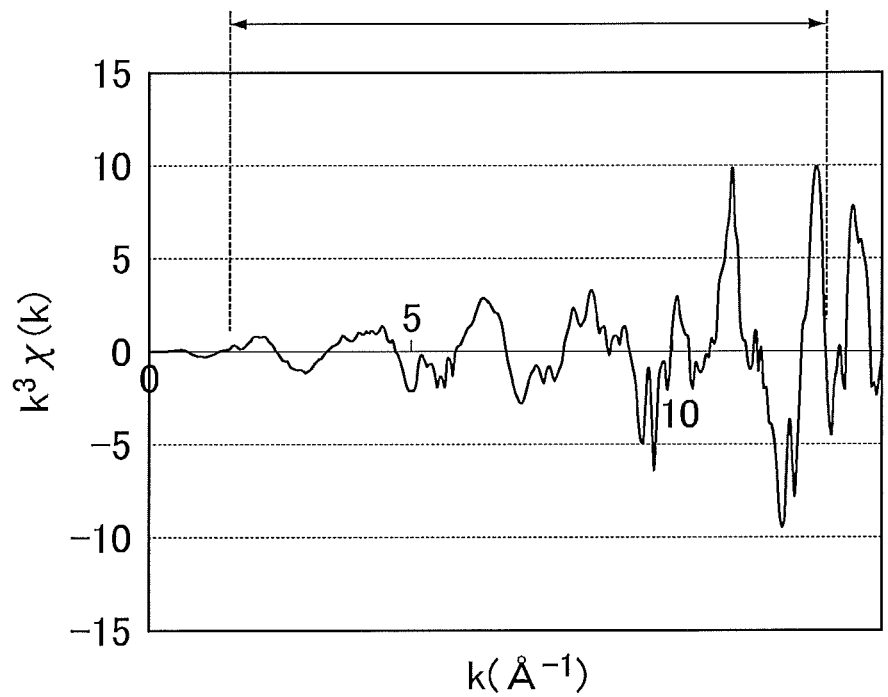
FIG. 3 is a graph showing a spectrum obtained by multiplying the EXAFS oscillation spectrum extracted in Example 1 by $k^3$.

FIG. 2 shows the obtained EXAFS oscillation in k-space. As shown in FIG. 2, oscillation decreases as the k value increases, which makes the analysis difficult. Therefore, x(k) was multiplied (weighted) by $k^3$. FIG. 3 shows a spectrum after this multiplication.

In order to determine the distance between atoms or coordination number, the k-space representation needs to be transformed into a real space representation. As shown in FIG. 3, noise increases as the k value increases. Therefore, Fourier transformation was performed on the range free of noisy portions, that is, the range indicated by the double-headed arrow in FIG. 3, to produce a radial distribution function in real space for the rubber sample.

The Fourier transformed spectrum was then inverse-Fourier transformed to obtain an actual EXAFS oscillation $E_{exp}(k)$. The obtained spectrum corresponds to the spectrum of FIG. 3 from which noise was eliminated.

(2) Reverse Monte Carlo (RMC) Calculation

The three-dimensional structure of sulfur atoms in the rubber sample was determined by the reverse Monte Carlo method from the actual EXAFS oscillation $E_{exp}(k)$.

The reverse Monte Carlo calculation was carried out in the following calculation conditions.
Program: RMC_POT
Initial configuration: 7400 particles were randomly placed.
Number density of sulfur atoms: The number density was determined as described later.

The $E_{calc}(k)$ used in the reverse Monte Carlo calculation was calculated from each three-dimensional configuration based on previous calculations using an ab initio self-consistent real space multiple scattering calculation program (FEFF) based on an all-electron, real space relativistic Green's function formalism.

The calculations were made under the following restrictions.
(i) The S—S interatomic distance is not shorter than 2.0 Å.
(ii) The coordination number of sulfur is 2.
(iii) The sulfur-sulfur bond angle is 120 to 145° as determined based on the results of molecular orbital calculations.

(3) Number Density of Sulfur Atoms

Chemicals that were not involved in the bonds in rubber, such as free sulfur (sulfur not involved in crosslinking), oil, wax, and antioxidants, were removed by Soxhlet extraction in accordance with JIS K6229. Specifically, an extraction flask provided at the lowermost portion of a Soxhlet extractor was filled with acetone, and 20 mg of the rubber sample finely cut with scissors was put on a paper or in a sintered glass container, which were provided at the center portion, and a condenser was connected to the uppermost portion. Then extraction was performed for 24 hours.

After the removal of chemicals not involved in the bonds in rubber by the extraction, the amount of sulfur atoms (% by mass) involved in crosslinking was determined in accordance with JIS K6222, "Rubber compounding ingredients—Sulfur—Methods of test".

In addition, after the removal of chemicals not involved in the bonds in rubber by the extraction, the density of the rubber sample was measured in accordance with JIS 28807, "Methods of measuring density and specific gravity of solid".

The number density of sulfur atoms [atoms/Å$^3$] in the rubber sample was determined from the amount of sulfur atoms involved in crosslinking and the density of the rubber sample.

(4) Calculation of Crosslink Density

Based on the three-dimensional structure of sulfur atoms in the rubber sample determined as above, the number of sulfide bonds for each of different sulfide bonds having 1 to 8 sulfur atoms (R—S$_n$—R (1≤n≤8)) was counted, and then the crosslink densities of the different sulfide bonds (R—S$_n$—R (1≤n≤8)) were calculated according to the formula (3) below. Table 1 shows the crosslink densities of the sulfide bonds.

Since a structurally stable polysulfide bond determined by molecular orbital calculations was found to have an S—S interatomic distance of 2.0 to 2.4 Å, sulfur atoms with an S—S interatomic distance of 2.0 to 2.4 Å were considered to form a sulfur-sulfur bond.

$$\text{Crosslink density [mol/cm}^3\text{]} = \frac{\text{Number of bonds}}{6.02 \times 10^{23} \times (\text{Side of BOX [cm]})^3} \quad (3)$$

The size of the BOX in the formula (3) is automatically determined from the number density of sulfur atoms in the rubber sample and the number of particles set in the reverse Monte Carlo calculation.

Comparative Example 1

(1) Preparation of Measurement Sample

A test piece (2 cm×2 cm, thickness 1 mm) of the obtained rubber sample was immersed in a solution mixture of tetrahydrofuran and toluene (1:1) for a day to allow the test piece to swell. The resulting swollen sample is identified as sample (a).

Separately, a test piece (2 cm×2 cm, thickness 1 mm) of the obtained rubber sample was immersed for a day in a solution mixture of tetrahydrofuran and toluene (1:1) in which an excess amount of lithium aluminum hydride (LiAlH$_4$) was dissolved, to allow the test piece to swell. The resulting swollen sample is identified as sample (b).

(2) Thermomechanical Analysis (TMA)

The compressive properties of the swollen rubber samples (a) and (b) were measured using a thermomechanical analyzer (product name "TMA-50", produced by SHIMADZU CORPORATION).

(3) Calculation of Crosslink Density

Using the Flory-Rehner equation, the total crosslink density vT, including all crosslinks, was calculated from the compressive properties of the swollen rubber sample (a), and the crosslink density vM of monosulfide bonds (R—S$_1$—R) was calculated from the compressive properties of the swollen rubber sample (b). Then the difference between vT and vM was determined and used as crosslink density vP (vP=vT−vM) of polysulfide bonds (R—S$_n$—R (2≤n≤8)) including disulfide bonds. Table 1 shows the results.

TABLE 1

| | Measurement | Crosslink density [mol/cm$^3$] of sulfide bond (R—S$_n$—R) | | | | | | | |
|---|---|---|---|---|---|---|---|---|---|
| | method | n = 1 | n = 2 | n = 3 | n = 4 | n = 5 | n = 6 | n = 7 | n = 8 |
| Ex. 1 | XAFS + RMC | 8.67 × 10$^{-5}$ | 1.53 × 10$^{-4}$ | 8.44 × 10$^{-5}$ | 2.52 × 10$^{-5}$ | 8.55 × 10$^{-6}$ | 2.31 × 10$^{-6}$ | 8.64 × 10$^{-7}$ | 1.15 × 10$^{-6}$ |
| Com. Ex. 1 | TMA | 6.43 × 10$^{-5}$ | | | | 1.29 × 10$^{-5}$ | | | |

As seen from the results of Table 1, the following was demonstrated in Example 1 using a method of measuring crosslink densities in a sulfur-containing polymer composite material, which comprises a measurement step of irradiating the sulfur-containing polymer composite material with high intensity X-rays and measuring an X-ray absorption spectrum of the composite material while varying the energy of the X-rays; a visualization step of determining the three-dimensional structure of sulfur atoms in the sulfur-containing polymer composite material by the reverse Monte Carlo method from the X-ray absorption spectrum; and a calculation step of calculating, from the three-dimensional structure of sulfur atoms, a crosslink density for each number of sulfur atoms bonded: a crosslink density for each number of sulfur atoms bonded was calculated from the three-dimensional structure of sulfur atoms in the sulfur-containing polymer composite material determined by the reverse Monte Carlo method, and thus more detailed information on the crosslink densities in the sulfur-containing polymer composite material was obtained than in the prior art.

The invention claimed is:

1. A method of measuring crosslink densities in a sulfur-containing polymer composite material, the method comprising:

a measurement step of irradiating the sulfur-containing polymer composite material with high intensity X-rays and measuring an X-ray absorption spectrum of the composite material while varying the energy of the X-rays;

a visualization step of determining a three-dimensional structure of sulfur atoms in the sulfur-containing polymer composite material by a reverse Monte Carlo method from the X-ray absorption spectrum;

a calculation step of calculating, from the three-dimensional structure of sulfur atoms, a crosslink density for each number of sulfur atoms bonded; and a determination step of determining the sulfur crosslinked structure of the sulfur-containing polymer composite material based on the calculated crosslink density for each number of sulfur atoms bonded.

2. The method according to claim 1, wherein, in the measurement step, the composite material is scanned with the X-rays in an energy range of 2300 to 4000 eV to measure an X-ray absorption spectrum near the K-shell absorption edge of sulfur.

3. The method according to claim 1, wherein, in the measurement step, the X-rays have a number of photons of $10^7$ photons/s or more, and a brilliance of $10^{10}$ photons/s/mrad$^2$/mm$^2$/0.1% bw or higher.

* * * * *